United States Patent [19]

Pathak et al.

[11] Patent Number: 5,081,153

[45] Date of Patent: Jan. 14, 1992

[54] STERILE PARENTERAL COMPOSITION

[75] Inventors: Ram D. Pathak, Epsom Downs; Ian P. O'Brien, Tadworth, both of England

[73] Assignee: Beecham Group p.l.c., Brentford, England

[21] Appl. No.: 26,010

[22] Filed: Mar. 16, 1987

Related U.S. Application Data

[63] Continuation of Ser. No. 734,614, May 16, 1985, abandoned.

[51] Int. Cl.⁵ .................. A61K 31/165; A61K 49/00; A61K 33/24
[52] U.S. Cl. ...................................... 514/619; 424/10; 424/649
[58] Field of Search ......................................... 514/619

[56] References Cited

U.S. PATENT DOCUMENTS 4,536,386  8/1985  Keenan ................................ 514/619

FOREIGN PATENT DOCUMENTS

36837/78  8/1981  Australia ............................. 514/619
52687/79  4/1983  Australia ............................. 514/619
52688/79  4/1983  Australia ............................. 514/619

OTHER PUBLICATIONS

The Pharmaceutical Codex, 11th Ed., 1979, The Pharmaceutical Press, pp. 566-567.
The Merck Index, 9th Ed., pp. 801-802.
1983 Physicians' Desk Reference, 37th Ed., pp. 428 and 1634-1635.
1983 Physicians' Desk Reference, 37th Ed., Supplement B, pp. B19-B21.
1984 Physicians' Desk Reference, 38th Ed., pp. 429 and 1607-1608.
251 Jama 6 (Feb. 19, 1984).
251 Jama 24, p. 3249 (Jun. 22/29 1984).
5 Im 4, pp. 70-72 (Apr. 1984).
Consultant, p. 16 (Dec. 1984).
Cancer (Jun. 1, 1984).
1985 Physicians' Desk Reference, 39th Ed., pp. 1659-1661.
42 Am. J. Hosp. Pharm. 1 (Jan. 1985).
1986 Physicians' Desk Reference, 40th Ed., pp. 1463-1465.
1987 Physicians' Desk Reference, 41st Ed., pp. 424 and 1634-1636.
1988 Physicians' Desk Reference, 42nd Ed., pp. 424 and 1696-1698.

*Primary Examiner*—Jerome D. Goldberg
*Attorney, Agent, or Firm*—Hopgood, Calimafde, Kalil, Blaustein & Judlowe

[57] ABSTRACT

A parenteral pharmaceutical composition comprising metoclopramide or a pharmaceutically acceptable salt thereof, and from 0 to 0.06% by weight, preferably from 0 to 0.006% by weight, of the composition of sodium metabisulphite, in combination with a pharmaceutically acceptable liquid carrier.

The use of this composition to alleviate nausea and vomiting, particularly in that associated with cancer chemotherapy is described.

17 Claims, No Drawings

STERILE PARENTERAL COMPOSITION

This application is a continuation of Ser. No. 06/734,614, filed May 16, 1985, now abandoned.

The present invention relates to a pharmaceutical composition containing metoclopramide, and its use in medicine.

Metoclopramide is a known anti-emetic agent which is used to alleviate nausea and vomiting. Hitherto, it has been administered by oral and injection routes, and for the latter use it has conveniently been packaged into 2 ml ampoules for injection, each ampoule containing 10 mg metoclopramide in saline solution. It has also been found necessary to include an effective level of the antoxidant sodium metabisulphite in the injectable composition to maintain stability.

Recently, the injectable composition has been used in association with certain types of cancer chemotherapy in which an anti-cancer agent such as Cisplatin is administered, and where a side effect of such treatment is severe nausea and vomiting. However, Cisplatin has been found to be incompatible with sodium metabisulphite, and this has limited the extent to which metoclopramide can be used in the chemotherapy treatment.

We have now found that, surprisingly, sodium metabisulphite can be omitted from the injectable composition without unduly affecting the stability of the composition, and that as a result larger ampoules, of up to 20 ml in size, can be employed in combination with Cisplatin in infusion for the chemotherapy treatment. It is also possible to include small amounts of sodium metabisulphite, substantially less than the 0.15% by weight of metabisulphite hitherto employed in the 2 ml ampoule size, without having compatibility problems with Cisplatin.

Accordingly, the present invention provides a parenteral pharmaceutical composition comprising metoclopramide or a pharmaceutically acceptable salt thereof and from 0 to 0.06% by weight of the composition of sodium metabisulphite, in combination with a pharmaceutically acceptable liquid carrier.

Preferably the amount of sodium metabisulphite present is from 0% to 0.006% by weight of the composition and most preferably 0% of sodium metabisulphite is present.

Examples of a pharmaceutically acceptable salt of metoclopramide include the hydrochloride.

Preferably, the liquid carrier comprises sterile saline solution.

The amount of metoclopramide administered to a patient should be sufficient to exert an anti-emetic effect. An anti-emetically effective amount of metoclopramide will depend on a number of factors such as the severity of the emesis being treated and the body weight of the patient. However in general a dosage of from 0.014 mg/kg to 10 mg/kg per day will be administered to a human.

Suitably the composition is in a unit dosage form, such as an ampoule, preferably containing an anti-emetically effective amount of metoclopramide. A unit dose in excess of 1 mg, in particular in excess of 10 mg, for a 70 kg adult will have an anti-emetic effect. For the sever emesis caused by cancer chemotherapy, such as by Cisplatin therapy, however, a unit dose of 50 to 200 mg, in particular about 100 mg, is preferred. The volume of the unit dose may be from 1 ml to 40 ml, in particular from 2 ml to 20 ml, the smaller volumes correlating with the smaller dosage units and the larger volumes with the larger dosage units. The larger volumes are thus most suitable for use in cancer chemotherapy such as Cisplatin therapy.

The unit dose may be administered from once a day to as many times as is necessary to give a dosage in 24 hours of from 0.014 to 10 mg/kg bodyweight. Thus for example in the aforementioned Cisplatin therapy, a 100 mg unit dose of metoclopramide may suitably be administered from 1 to 7 times in a 24 hour period to a 70 kg adult.

The composition of the invention may be prepared by admixing the components in conventional manner.

Further according to the present invention there is provided a method of treating nausea and vomiting which comprises administering to a patient in need thereof an anti-emetically effective amount of a composition of the invention.

The invention is now illustrated by means of the following Example.

EXAMPLE

The following formulations were made up as follows:

| Formulation 1 | |
|---|---|
| | % w/v |
| Metoclopramide hydrochloride BP | 0.526 |
| Sodium chloride BP | 0.800 |
| Water for injection BP | to 100.000 |

| Formulation 2 | |
|---|---|
| Metoclopramide hydrochloride BP | 0.526 |
| Sodium chloride BP | 0.800 |
| Sodium metabisulphite | 0.006 |
| Water for injection BP | to 100.000 |

PREPARATION 1

The sodium chloride, sodium metabisulphite where present and the metoclopramide hydrochloride were dissolved in that order in boiled water for injection BP (about 80% final volume) at below 30° C. under stirring and with nitrogen bubbled through the water. The solution was made up to the final volume with water for injection at below 30° C. The solution was filtered under nitrogen pressure through a 5 um filter, collected and filled into 20 ml glass ampoules under nitrogen. The product was sterilised by heat treatment of the sealed ampoules in an autoclave.

PREPARATION 2

The above procedure was repeated except that the final solution was filtered through a sterilising filter, and the filling was effected in a sterile area.

We claim:

1. A sterile parenteral pharmaceutical composition consisting essentially of an anti-emetically effective amount of metoclopramide or a pharmaceutically acceptable salt thereof, and from 0 to 0.06% by weight of the composition of sodium metabisulphite, in combination with a pharmaceutically acceptable liquid carrier, in non-extemporaneous form.

2. A composition according to claim 1 which contains from 0 to 0.006% by weight of the composition of sodium metabisulphite.

3. A composition according to claim 1 wherein the metoclopramide is in the form of the hydrochloride salt.

4. A composition according to claim 1 wherein the composition is in unit dosage form and contains at least 1 mg of metoclopramide or a pharmaceutically acceptable salt thereof.

5. A composition according to claim 4 wherein the unit dosage form contains from 50 to 200 mg of metoclopramide or a pharmaceutically acceptable salt thereof.

6. A composition according to claim 5 wherein the unit dosage contains 100 mg of metoclopramide or a pharmaceutically acceptable salt thereof.

7. A composition according to claim 4 wherein the volume of the unit dosage is from 1 ml to 40 ml.

8. A composition according to claim 7 wherein the volume of the unit dosages is from 2 ml to 20 ml.

9. A method of treating nausea and vomiting which comprises administering to a patient in need thereof on anti-emetically effective amount of a composition according to claim 1.

10. A sterile parenteral pharmaceutical composition, comprising an anti-emetically effective amount of metoclopramide, or a pharmaceutically acceptable salt thereof, and essentially 0% by weight of sodium metabisulphite, in combination with a pharmaceutically acceptable liquid carrier.

11. A composition according to claim 10 wherein the metoclopramide is in the form of the hydrochloride salt.

12. A composition according to claim 10 wherein the composition is in unit dosage form and contains at least 1 mg of metoclopramide or a pharmaceutically acceptable salt thereof.

13. A composition according to claim 12 wherein the unit dosage form contains from 50 to 200 mg of metoclopramide or a pharmaceutically acceptable salt thereof.

14. A composition according to claim 13 wherein the unit dosage contains 100 mg of metoclopramide or a pharmaceutically acceptable salt thereof.

15. A composition according to claim 12 wherein the volume of the unit dosage is from 1 ml to 40 ml.

16. A composition according to claim 15 wherein the volume of the unit dosages is from 2 ml to 20 ml.

17. A method of treating nausea and vomiting which comprises administering to a patient in need thereof an anti-emetically effective amount of a composition according to claim 10.

* * * * *

UNITED STATES PATENT AND TRADEMARK OFFICE
CERTIFICATE OF CORRECTION

PATENT NO. : 5,081,153
DATED : January 14, 1992
INVENTOR(S) : Ram D. Pathak and Ian P.O'Brien It is certified that error appears in the above-identified patent and that said Letters Patent is hereby corrected as shown below:

On the cover page, after the "Related U.S. Application Data"

add --

[30]    Foreign Application Priority Data

May 17, 1984 [GB] United Kingdom .............. 8412585--

Signed and Sealed this

Twenty-first Day of September, 1993

Attest:

BRUCE LEHMAN

Attesting Officer     Commissioner of Patents and Trademarks